United States Patent [19]

Siverson

[11] 4,015,594
[45] Apr. 5, 1977

[54] RECORDING SPHYGMOMANOMETER SPHYGPRESSURE GRAPH

[76] Inventor: Lilian Ellen Siverson, 3784 Spruce St., Burnaky, BC V5G, 1X9, Canada

[22] Filed: June 14, 1976

[21] Appl. No.: 696,039

[52] U.S. Cl. .................. 128/2.05 G; 128/2.05 Q; 346/33 ME; 346/139 R
[51] Int. Cl.² .......................................... A61B 5/02
[58] Field of Search ............... 128/2.05 G, 2.05 Q, 128/2.05 M, 2.05 C, 2.05 A; 346/33 ME, 139 R, 72

[56] References Cited

UNITED STATES PATENTS

| 183,205 | 10/1876 | Pond | 128/2.05 G |
|---|---|---|---|
| 205,412 | 6/1878 | Pond | 128/2.05 G |
| 1,043,521 | 11/1912 | Hoobler | 128/2.05 G |
| 2,753,863 | 7/1956 | Bailey | 128/2.05 G |
| 3,314,295 | 4/1967 | Wukovitz | 346/72 X |
| 3,662,394 | 5/1972 | Dudler | 346/21 |
| 3,754,545 | 8/1973 | Weinstein | 128/2.05 Q |
| 3,771,515 | 11/1973 | Hurwitz | 128/2.05 G |

*Primary Examiner*—Kyle L. Howell
*Attorney, Agent, or Firm*—Albert W. Hilburger

[57] ABSTRACT

A sphygpressure graph of the aneroid gauge type including a housing, connected with a sphygmocuff, supporting a series of telescoping tubes, connected in right angular relation, and a stylus, mounted on the endmost tube, movable over a chart to scribe the blood pressures. A ratchet and pawl arrangement engaging the telescoping tubes prevents reciprocating action of pulse pressure moving the stylus in a to and fro movement transversely over a graph paper but records the pulse by longitudinally scribing a graph paper during release of pressure from the sphygmocuff.

1 Claim, 5 Drawing Figures

RECORDING SPHYGMOMANOMETER SPHYGPRESSURE GRAPH

BACKGROUND OF THE INVENTION

This is a substitute of application Ser. No. 365,811 filed May 31, 1973, now abandoned.

The present invention relates to aneroid pressure gauges of the type used in a sphygmomanometer for clinical blood pressure determinations and to means for easily forming a permanent record of pulse readings.

The measurement of blood pressure is normally obtained by the use of sphygmomanometer generally comprising an inflatable cuff or sleeve for applying pressure to an artery. A mercury-gravity manometer or an aneroid manometer inflating bulb is used to generate air pressure in the cuff including a valve for bleeding off air pressure at any desired rate. Additionally, a stethoscope is used to hear the Korotkov sounds. Blood pressure determination, with such equipment, is made by increasing air pressure in the cuff until arterial flow is completely stopped. The bleed off valve is then opened to permit deflation of the cuff until blood begins to flow again and the onset of the Korotkov sounds is heard in the stethoscope. The pressure at which this event occurs is the systolic pressure and its magnitude is noted. As air pressure in the cuff is further reduced, blood flow is impeded by the cuff pressure proportionally less during each heart cycle until the blood flow becomes continuous and the Korotkov sounds disappear. This pressure is the diastolic pressure and is noted. While obtaining blood pressure readings in the foregoing manner it is necessary to focus attention simultaneously on the threshold or disappearance of sound in the stethoscope and on the moving display of the declining pressure function by the mercury-gravity manometer or pointer of an aneroid manometer. When once observed it is necessary to remember the pressures at which the Korotkov sounds appear and disappear until the measurement has been completed and they can be written. These observations and memory functions to obtain accurate blood pressure readings must be performed by trained personnel, and even then sometimes requires repeated measurements to obtain accurate readings.

The principle feature of this invention resides in its simplicity of construction and simplicity of operation wherein personnel with little or no training may easily learn to operate the syphgmograph and obtain a permanent record of blood pressure reading to be added to the patient's record.

SUMMARY OF THE INVENTION

A box-like housing is secured to the outer surface of an inflatable blood restricting cuff or sleeve. The housing is provided with an aperture communicating with the interior of the sleeve. A plurality of telescoping tubular members communicates with the housing aperture with the free end of the end-most tube being provided with a stylus slidably contacting a graph paper supported by the housing and removable therefrom. Spring means adjustably regulate telescopic extension and retraction movement of the telescoping tubes in response to air pressure applied to the tubes from the cuff or sleeve. Ratchet and pawl means, supported by the housing and telescoping tubes limit telescopic movement of the tubes to a movement which records the pulse.

The principle object of this invention is to provide a sphygpressure graph for forming a permanent record of the pulse or heart throb motion of a patient to eliminate estimations or guesswork and obtain an accurate recording of blood pressure without the use of a stethoscope which may be easily used by persons having little or no technical training in its operation.

It is to be understood that both the foregoing general description and the following detailed description are exemplary and explanatory but are not restrictive of the invention.

The accompanying drawings which are incorporated in, and constitute a part of this invention, illustrate preferred embodiments of the invention, and together with the description, serve to explain the principles of the invention.

OF THE DRAWINGS

DESCRIPTION OF THE PREFERRED EMBODIMENTS

Like characters of reference designate like parts in those figures of the drawings in which they occur.

Figure 1:
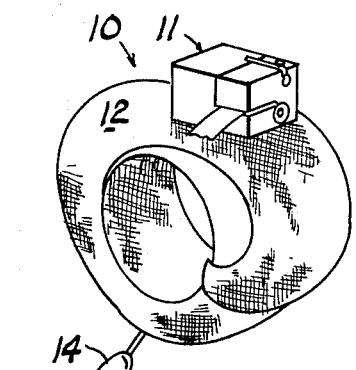
FIG. 1 is a perspective view of the device in operative position connected with a blood-flow-restricting sleeve.

Referring initially to FIG. 1, the reference numeral 10 indicates the device, as a whole, comprising a housing 11 rectangular in general configuration which is secured to the normally outwardly disposed surface of a blood-flow-restricting cuff or sleeve 12 having a flexible bulb 14 connected therewith and provided with a release valve 16 for pumping air into and releasing air under pressure from the sleeve. The sleeve 12 is substantially conventional preferably formed to provide a pliable plastic material for its outer surface while the interior patient contacting surface is preferably formed of soft material.

Figure 2:
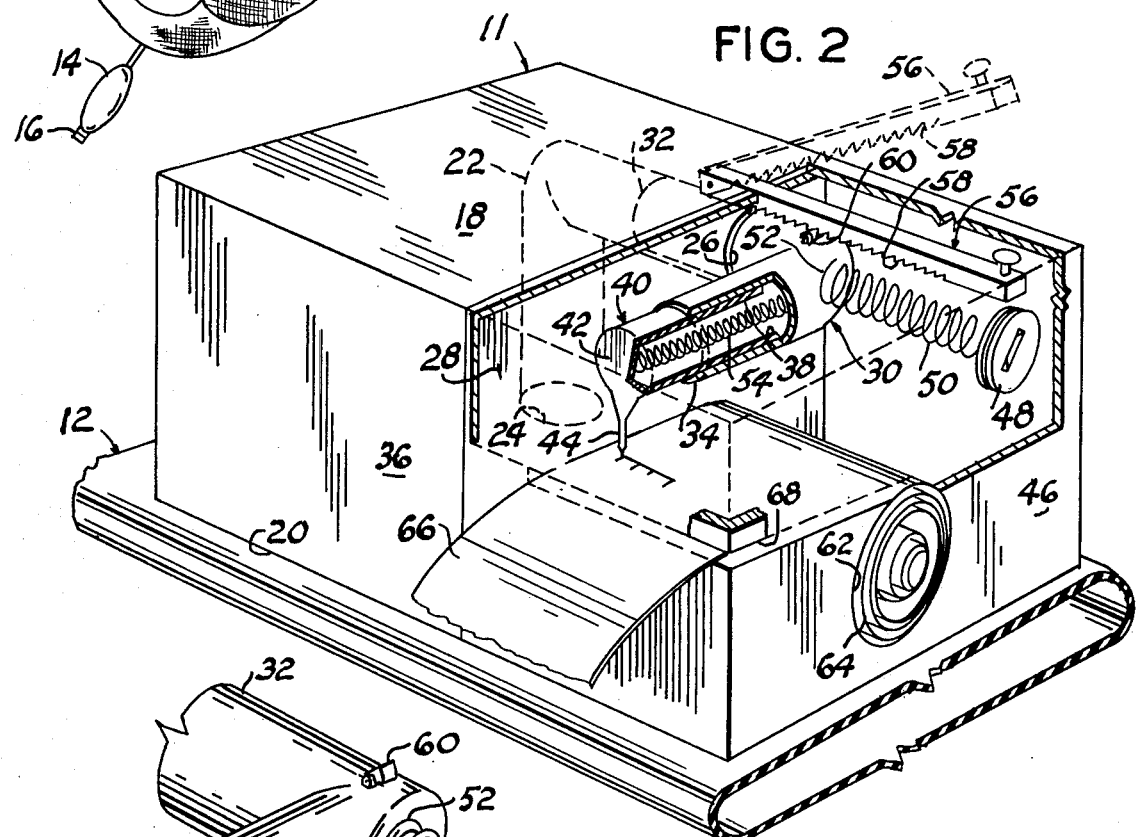
FIG. 2 is a fragmentary perspective view, to an enlarged scale, of the device having parts broken away and shown by dotted lines, for clarity.

Turning now to FIG. 2, the housing 11 is provided with an upper surface 18 parallel with its bottom surface 20 which is secured, as by bonding it to the normally outwardly disposed surface of the sleeve 12. One end portion of the housing 11 is provided with a right angular aperture 22 opening through the bottom wall 20 and communicating, at one end 24, with the interior of the sleeve 12 and opening at its other end 26 through an intermediate partition or transverse wall surface 28 of the box-like housing. Obviously the aperture 22 may comprise a tube if preferred.

Figure 3:
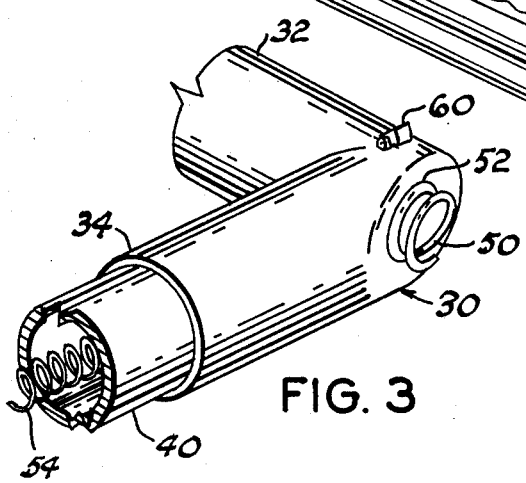
FIG. 3 is a fragmentary perspective view, to a further enlarged scale, of two of the telescoping tubes.

A right-angular shaped tube 30 (FIGS. 2 and 3) has one end portion 32 telescopically received by the aperture end opening 26 for to and fro movement of this end portion in a direction parallel with the longitudinal axis of the sleeve 12 and with the upper and lower surfaces of the housing. The other end portion 34 of the tube 30 projects toward the housing lateral side 36 and telescopically receives one end portion 38 of a scribing tube 40 having its other end closed by an end plate 42 and secured to a depending stylus 44.

With continued reference to FIG. 2, the end wall 46 of the housing 11, parallel with the intermediate wall 28, threadedly supports a spring retainer 48 having one end of a first helical spring 50 connected thereto with the other end 52 of the spring bearing against the right angular tube 30 with the longitudinal axis of the spring 50 coaxially aligned with the end portion 32 of the tube 30. A second helical spring 54 is coaxially contained by the telescoping tube end portion 38 of the tube 40 with the respective ends of the second spring 54 bearing against the inner wall surface of the tube 30 and the tube end plate 42. The second spring 54 normally tends to telescope the tube 40 into the tube end portion 34.

A rack 56 (FIG. 2), comprising an elongated arm hingedly connected at one end to the housing within a suitable recess formed in its upper surface longitudinally overlies the tube end portion 32 and first spring 50 and is manually movable vertically about the axis of its hinged connection. Intermediate its ends the arm is provided with a series of depending ratchet teeth 58 normally engaged by a pawl 60 pivotally connected to the upper surface of the right angular tube 30 so that the pawl and rack prevents longitudinal to and fro movement of the tube end portion 32 for reasons presently explained.

The housing is further provided with a cylindrical socket 62 extending inwardly from its end wall 46 for receiving a roll of graph paper 64, or the like, with the unwound end portion 66 of the graph paper being slidably received by a slot 68 formed in the housing side wall 36 and end wall 46 permitting the paper to be progressively drawn out of the slot and separated from the remainder of the roll.

Figure 4:
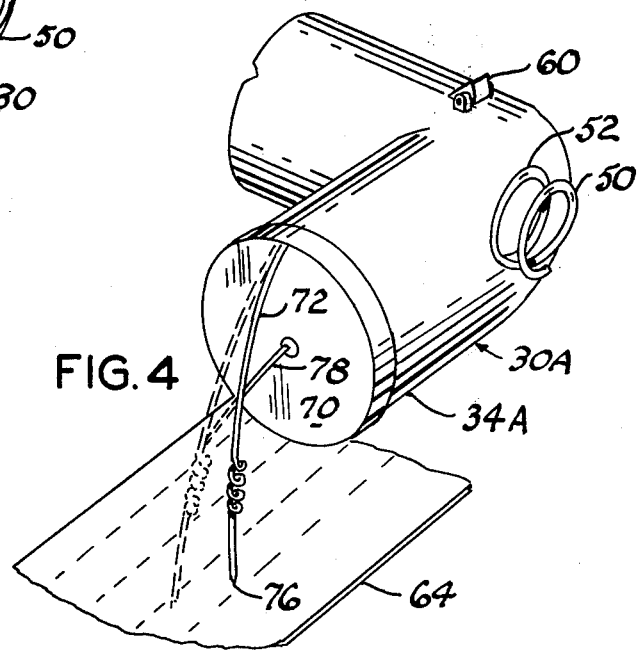
FIG. 4 is a fragmentary perspective view, to a further enlarged scale, similar to FIG. 3, illustrating another embodiment using a stylus operated membrane connected with one of the telescoping tubes; and, FIG. 5 is a fragmentary top view of the graph record formed illustrating two examples of blood pressure readings obtained by the device.

Referring now to FIG. 4, a modified form of the right-angular tube is shown at 30A which eliminates the spring 54 and telescoping action of the tube 40 and substitutes a diaphragm-like cap 70 which closes the end of the right-angular tube portion 34A. The cap 70 is provided with a stylus arm or stem 72 having spring-like expansion coils 74 intermediate its end for maintaining its stylus tip 76 in contact with the graph paper 64. The stylus is moved in response to pulse pressure within the tube 30A by an arm 78 coaxially connected at one end with the cap 70 and connected at its other end with the stem 72 intermediate its end.

Operation

In operation the device 10 is positioned, as illustrated in FIG. 1, around a patient's arm, not shown. The sleeve 12 is inflated in the normal manner by the use of the bulb 14. When the sleeve is inflated the air therein under greater than atmospheric pressure enters the housing aperture 22 and telescoping tubes 30 and 40 extending the right angular tube 30 toward the housing wall 46 compressing the spring 50. The telescoping tube 40 is also extended out of the right-angular tube end portion 34. When the pressure has fully extended the telescoping tubes the rack 56 is lowered into its groove so that its teeth 58 engage the pawl 60 thus preventing the pulse throb from pulsating the tube end portion 32 in a to and fro motion but permits the telescoping tube end portion 30 to be retracted into the housing aperture 22 in response to a reduction of air pressure within the sleeve and the force of the first spring 50. The pulsating action of the patient's pulse is thus transferred to the tube 40 which responds to the pulsations and moves the stylus 44 as illustrated.

Figure 5:
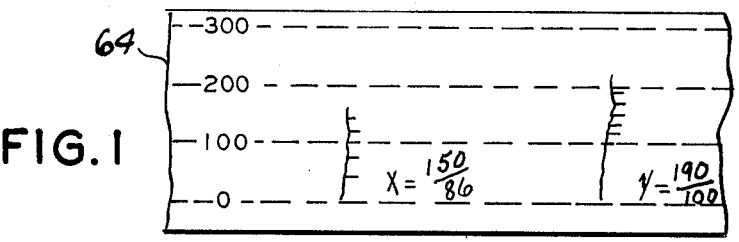

FIG. 5 illustrates a fragment of the graph paper 64 marked by the stylus 44 wherein two blood pressure readings labled X and Y are recorded. The short marks of each example each indicate a pulse while the continuous transverse mark or line of each example indicates release of air pressure from the sleeve 12.

The invention, in its broader aspects is not limited to the specific details shown and described, and departures may be made from such details without departing from the principles of the invention, and without sacrificing its chief advantages.

What is claimed is:
1. A blood-pressure-measuring device, comprising:
   a blood-flow-restricting sleeve;
   pump means for pressurizing said sleeve;
   a housing secured to said sleeve, said housing having an aperture communicating with the interior of said sleeve;
   a right-angular tube telescopically received at one end portion within the housing aperture;
   a first spring normally biasing said one end portion of said right-angular tube into the aperture;
   ratchet means including a rack pivotally supported by said housing in overlying relation with respect to said one end portion of said right-angular tube, said rack having a series of ratchet teeth projecting toward said right-angular tube;
   a pawl secured to said right-angular tube and engaged by said ratchet teeth permitting telescopic movement of said right-angular tube into the housing aperture and preventing telescopic extending movement of said right-angular tube out of the housing aperture;
   a scribing tube having one closed end and having its open end telescopically received within the other end portion of said right-angular tube;
   a second spring within said scribing tube normally biasing said scribing tube into said other end portion of said right-angular tube;
   graph paper supported by said housing; and
   a stylus secured to the closed end of said scribing tube and contacting said graph paper.

* * * * *